US012678359B2

(12) United States Patent
Sun

(10) Patent No.: US 12,678,359 B2
(45) Date of Patent: Jul. 14, 2026

(54) INTELLIGENT ANIMAL OPERATION TABLE

(71) Applicant: Jiayi Sun, Shanghai (CN)

(72) Inventor: Jiayi Sun, Shanghai (CN)

( * ) Notice: Subject to any disclaimer, the term of this patent is extended or adjusted under 35 U.S.C. 154(b) by 302 days.

(21) Appl. No.: 18/643,492

(22) Filed: Apr. 23, 2024

(65) Prior Publication Data

US 2025/0082452 A1 Mar. 13, 2025

(30) Foreign Application Priority Data

Sep. 11, 2023 (CN) .......................... 202322464708.X

(51) Int. Cl.
| | |
|---|---|
| *A61G 13/00* | (2006.01) |
| *A61B 5/00* | (2006.01) |
| *A61B 5/388* | (2021.01) |
| *A61B 50/10* | (2016.01) |
| *A61B 90/10* | (2016.01) |
| *A61B 90/35* | (2016.01) |

(Continued)

(52) U.S. Cl.
CPC .............. *A61G 13/00* (2013.01); *A61B 5/388* (2021.01); *A61B 5/4064* (2013.01); *A61B 5/704* (2013.01); *A61B 50/10* (2016.02); *A61B 90/10* (2016.02); *A61B 90/35* (2016.02); *A61B 2050/105* (2016.02); *A61B 2503/40* (2013.01); *A61D 13/00* (2013.01); *A61N 1/0529* (2013.01)

(58) Field of Classification Search
CPC ...... A61G 13/00; A61B 5/388; A61B 5/4064; A61B 5/704; A61B 2050/105
See application file for complete search history.

(56) References Cited

U.S. PATENT DOCUMENTS

| | | | | |
|---|---|---|---|---|
| 5,083,558 A | * | 1/1992 | Thomas ................... | F24F 3/163 |
| | | | | 128/202.16 |
| 6,467,112 B1 | * | 10/2002 | Cheng ...................... | A61D 3/00 |
| | | | | 5/606 |
| 9,192,457 B2 | * | 11/2015 | Keil ......................... | A61D 3/00 |

(Continued)

OTHER PUBLICATIONS

Wang et al. "Protocol for deep brain stimulation in the fimbria-fornix of freely moving mice", STAR Protocols 3, 101054; Mar. 18, 2022; pp. 1-18. (Year: 2022).*

(Continued)

*Primary Examiner* — Angela M Hoffa
(74) *Attorney, Agent, or Firm* — DILWORTH IP, LLC

(57) ABSTRACT

An intelligent animal operation table is provided. An instrument cabinet is fixed at a rear part of a top surface of an operation platform through supporting columns; a brain stereotaxic instrument is fixed on a front side of the instrument cabinet; a physiological signal acquisition system is located below the instrument cabinet and behind the brain stereotaxic instrument; a welding table is located on the front side of the instrument cabinet and a right side of the physiological signal acquisition system; an electroneurographic signal amplification display is located on the front side of the instrument cabinet and on a right rear side of the welding table; and a shadowless lamp is fixed on a right part of a top surface of the instrument cabinet. The intelligent animal operation table is reasonable and compact in structural arrangement and is convenient for the complete implementation of a robot animal experiment.

10 Claims, 2 Drawing Sheets

(51) Int. Cl.
    *A61D 13/00*      (2006.01)
    *A61N 1/05*      (2006.01)

(56)              References Cited

U.S. PATENT DOCUMENTS

2006/0052689 A1*  3/2006  Scouten ................ G09B 23/30
                                             600/417
2009/0241262 A1* 10/2009  Jehn .................... A61G 13/102
                                           5/607

OTHER PUBLICATIONS

"SurgiSuite" Kent Scientific <https://kentscientific.com/products/surgisuite/> captured by Wayback Machine Feb. 21, 2022; 2 pages. (Year: 2022).*
"PhysioSuite" Kent Scientific <https://kentscientific.com/products/physiosuite/> captured by Wayback Machine Feb. 21, 2022; 5 pages. (Year: 2022).*
"Rodent Surgical Suites" University of Florida <https://acs.ufl.edu/rodent-surgical-suites/> captured by Wayback Machine Sep. 25, 2022; 4 pages. (Year: 2022).*

* cited by examiner

INTELLIGENT ANIMAL OPERATION TABLE

CROSS-REFERENCES TO RELATED APPLICATIONS

This application claims the priority to Chinese Patent Application No. 202322464708.X, filed on Sep. 11, 2023, the disclosure of which is incorporated herein by reference in its entirety.

FIELD OF THE INVENTION

The present invention relates to biomedical engineering experimental devices, and in particular to an intelligent animal operation table.

BACKGROUND OF THE INVENTION

An intelligent animal, also known as "animal robot" or "robot animal", controls the nervous system of the animal by an artificial electrical signal, so that the animal is changed into a "machine type" animal and can perform various complicated tasks according to human will. The robot animal has become one of the important research directions in the technical field of robots.

In 2007, the first robot bird in the world was successfully developed in Robot Research Center, Shandong University of Science and Technology. The motion principle of the robot bird is to stimulate some nerve sites of a pigeon with coded electrical signals, so that the pigeon can be reliably controlled and navigated to take off and fly along the expected route. The robot bird can be widely applied to various detection, aerial photography, delivery, bird colony research and exploration of areas inaccessible to human beings. In addition, the researches of robot animals also play an important role in promoting the development of clinical rehabilitation engineering and other related disciplines.

At present, the research in the field of robot animals is still at the laboratory level, and there are many important problems to be solved and improved. Therefore, experimental research is particularly important for the development and progress of the field of the robot animals. The robot animal technology belongs to the field of interdisciplinary research of information, robots and animal medicine, so robot animal operation experiments require complicated engineering tools and medical appliances. The common animal operation table is an ordinary animal operation table and is not suitable for robot animal experimental operations belonging to the interdisciplinary category. In the robot animal operation experiments, the engineering tools and the medical appliances are mixed and placed optionally, which will bring great inconvenience for experimenters.

SUMMARY OF THE INVENTION

The technical problem to be solved by the present invention is to provide an intelligent animal operation table, which is reasonable and compact in structural arrangement and is convenient for the complete implementation of a robot animal experiment.

To solve the above technical problem, the intelligent animal operation table provided by the present invention includes an operation platform 3, an instrument cabinet 6, a brain stereotaxic instrument 13, a physiological signal acquisition system 12, a welding table 11, an electroneurographic signal amplification display 9 and a shadowless lamp 5;

the instrument cabinet 6 is a cuboid, and a left end and a right end of a bottom surface of the instrument cabinet are fixed at a left end and a right end of a rear part of a top surface of the operation platform 3 respectively through supporting columns 64;

the brain stereotaxic instrument 13 is fixed on a left part of the top surface of the operation platform 3 and located on a front side of the instrument cabinet 6;

the physiological signal acquisition system 12 is fixed on the left part of the top surface of the operation platform 3 and located below the instrument cabinet 6 and behind the brain stereotaxic instrument 13;

the welding table 11 is fixed on the top surface of the operation platform 3 and located on the front side of the instrument cabinet 6 and a right side of the physiological signal acquisition system 12;

the electroneurographic signal amplification display 9 is fixed on a right part of the top surface of the operation platform 3, located on the front side of the instrument cabinet 6 and on a right rear side of the welding table 11, and configured to be in signal connection with an electroneurographic signal sensor of a corresponding brain function area of an animal; and the shadowless lamp 5 is fixed on a right part of a top surface of the instrument cabinet 6.

Preferably, the instrument cabinet 6 forms a left medical instrument cabinet 61 and a right electrical instrument cabinet 62 which are isolated from each other;

the medical instrument cabinet 61 is configured to store instruments used for craniotomy and electrode implantation operations; and the electrical instrument cabinet 62 is configured to store an electronic device and a circuit welding tool.

Preferably, the intelligent animal operation table further includes an ultraviolet disinfection lamp (7); and the ultraviolet disinfection lamp 7 is fixedly arranged in an upper part of the instrument cabinet 6.

Preferably, the intelligent animal operation table further includes a body temperature monitor 10; and the body temperature monitor 10 is fixed on the top surface of the operation platform 3 and located below the instrument cabinet 6 and behind the welding table 11.

Preferably, the intelligent animal operation table further includes a waste storage box 4; and the waste storage box 4 is fixed on a rear part of a left end face of the operation platform 3.

Preferably, the intelligent animal operation table is further provided with a mains power socket 8; and the mains power socket 8 is fixedly arranged on the top surface of the operation platform 3 and located behind the electroneurographic signal amplification display 9 and below the instrument cabinet 6.

Preferably, the welding table 11 includes a welding rotation base 111, a welding base 115 and a welding platform 112;

the welding base 115 is configured to be attached and fixed to the top surface of the operation platform 3;

an upper end of the welding rotation base 111 is connected to a bottom surface of the welding platform 112, and a lower end of the welding rotation base is connected to the welding base 115;

the welding platform 112 is capable of rotating around a vertical shaft relative to the welding base 115; and a top surface of the welding platform 112 is a concave surface with high front and rear parts and a low middle part.

Preferably, the welding table 11 further includes an electric soldering iron placing rack 113;

the electric soldering iron placing rack 113 is fixedly arranged on a rear end face of a right part of the welding platform 112; and a groove 114 is formed in the right part of the welding platform 112, and the groove 114 is used as a rosin pool.

Preferably, the intelligent animal operation table further includes a platform rotation base 2 and a base 1; and a bottom surface of the operation platform 3 is connected to the base 1 through the platform rotation base 2.

Preferably, the operation platform 3 is capable of rotating 270 degrees around the vertical shaft relative to the base 1 through the platform rotation base 2;

the physiological signal acquisition system 12 has 16 channels;

a cabinet door 63 of the instrument cabinet 6 is a push-pull cabinet door;

the instrument cabinet 6 and the operation platform 3 are made of a stainless steel material;

the welding platform 112 is capable of rotating 360 degrees around the vertical shaft relative to the welding base 115 through the welding rotation base 111; and the welding platform 112 is made of a marble material.

According to the intelligent animal operation table of the present invention, the instrument cabinet 6, the brain stereotaxic instrument 13, the physiological signal acquisition system 12, the welding table 11, the electroneurographic signal amplification display 9 and the shadowless lamp 5 are arranged on the operation platform 3; the instrument cabinet 6 is configured to store instruments used in operations; the brain stereotaxic instrument 13 is configured to realize animal brain localization and animal craniotomy and electrode implantation; the physiological signal acquisition system 12 is configured to acquire a plurality of physiological indexes for determining the physiological condition of animals; the welding table 11 is configured to realize the welding of an electronic circuit of the robot animal; the electroneurographic signal amplification display 9 is configured to observe and monitor an electroneurographic signal of an implanted electrode stimulating the corresponding brain function area of the animal to determine the correctness of the electrode implantation position; and the shadowless lamp 5 is configured to provide illumination for the operation. The intelligent animal operation table is reasonable and compact in structural arrangement and is convenient for the complete implementation of a robot animal experiment.

BRIEF DESCRIPTION OF THE DRAWINGS

To describe the technical solutions of the present invention more clearly, a brief description of the accompanying drawings required by the present invention will be provided below. Obviously, the accompanying drawings in the following description show merely some embodiments of the present invention. Those of ordinary skill in the art can also derive other accompanying drawings from these accompanying drawings without making creative efforts.

Figure 1:
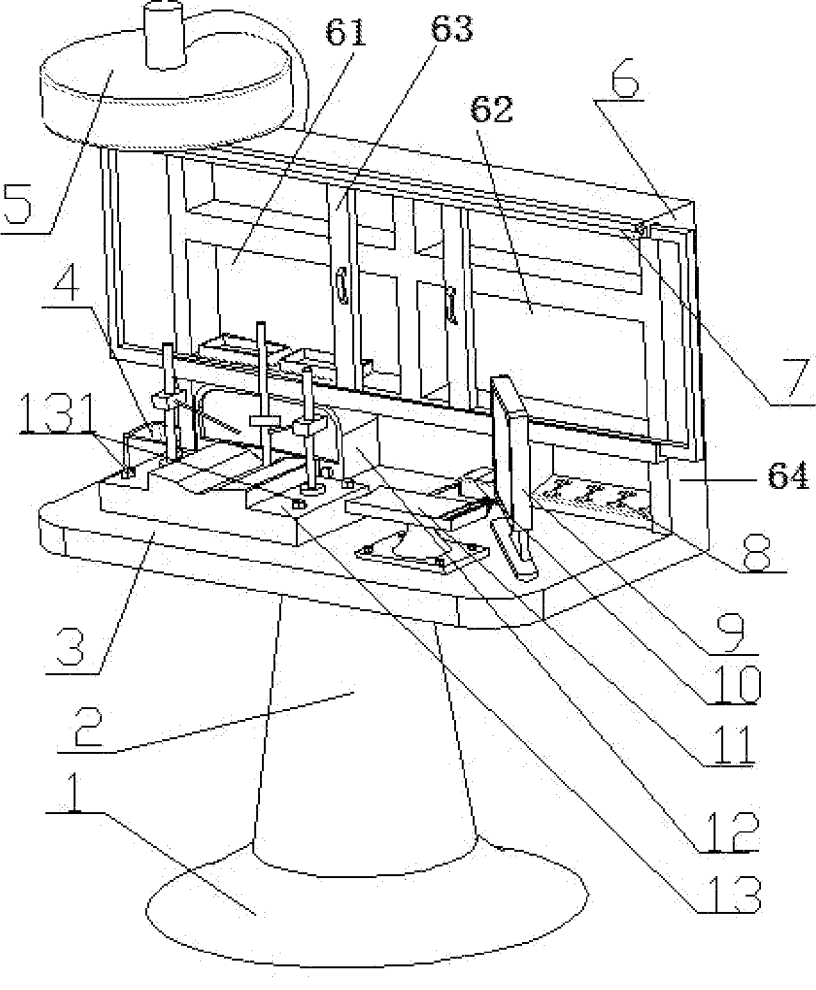
FIG. 1 is a schematic diagram of a three-dimensional structure according to an embodiment of an intelligent animal operation table of the present invention.

Description of reference numerals of the drawings: operation platform 3; instrument cabinet 6; supporting column 64; medical instrument cabinet 61; electrical instrument cabinet 62; cabinet door 63; brain stereotaxic instrument 13; physiological signal acquisition system 12; welding table 11; welding rotation base 111; welding base 115; welding platform 112; soldering iron placing rack 113; groove 114; electroneurographic signal amplification display 9; shadowless lamp 5; ultraviolet disinfection lamp 7; body temperature monitor 10; waste storage box 4; mains power socket 8; platform rotation base 2; base 1; bolt 131.

DETAILED DESCRIPTION

The technical solutions in the embodiments of the present invention are clearly and completely described below in conjunction with the drawings in the embodiments of the present invention. Apparently, the embodiments described are merely a part rather than all of the embodiments of the present invention. All other embodiments obtained by those of ordinary skills in the art without creative efforts based on the embodiments of the present invention shall fall within the protection scope of the present invention.

"First", "second" and other similar words used in the present invention do not indicate any order, quantity or importance, but are merely used to distinguish between different components. "Include", "comprise" or other similar words mean that an element or object appearing before the word contains elements or objects listed after the word and its equivalents, without excluding other elements or objects. "Connection", "connected" or other similar words are not limited to physical or mechanical connections, but can include electrical connections, whether direct or indirect. Terms "up", "down", "left", "right", "front", "rear" and the like are merely used to indicate relative position relations, and when the absolute position of a described object changes, the relative position may change accordingly.

It is to be noted that the embodiments and features in the embodiments of the present invention may be combined with each other without conflict.

Embodiment 1

As shown in FIG. 1, an intelligent animal operation table includes an operation platform 3, an instrument cabinet 6, a brain stereotaxic instrument 13, a physiological signal acquisition system 12, a welding table 11, an electroneurographic signal amplification display 9 and a shadowless lamp 5;

the instrument cabinet 6 is a cuboid, and a left end and a right end of a bottom surface of the instrument cabinet are fixed at a left end and a right end of a rear part of a top surface of the operation platform 3 respectively through supporting columns 64;

the brain stereotaxic instrument 13 is fixed on a left part of the top surface of the operation platform 3 and located on a front side of the instrument cabinet 6;

the physiological signal acquisition system 12 is fixed on the left part of the top surface of the operation platform 3 and located below the instrument cabinet 6 and behind the brain stereotaxic instrument 13;

the welding table 11 is fixed on the top surface of the operation platform 3 and located on the front side of the instrument cabinet 6 and a right side of the physiological signal acquisition system 12;

the electroneurographic signal amplification display 9 is fixed on a right part of the top surface of the operation platform 3, located on the front side of the instrument cabinet 6 and on a right rear side of the welding table 11, and configured to be in signal connection with an electroneurographic signal sensor of a corresponding brain function area of an animal; and the shadowless lamp 5 is fixed on a right part of a top surface of the instrument cabinet 6.

According to the intelligent animal operation table of Embodiment 1, the instrument cabinet 6, the brain stereotaxic instrument 13, the physiological signal acquisition system 12, the welding table 11, the electroneurographic signal amplification display 9 and the shadowless lamp 5 are arranged on the operation platform 3; the instrument cabinet 6 is configured to store instruments used in operations; the brain stereotaxic instrument 13 is configured to realize animal brain localization and animal craniotomy and electrode implantation; the physiological signal acquisition system 12 is configured to acquire a plurality of physiological indexes for determining the physiological condition of animals; the welding table 11 is configured to realize the welding of an electronic circuit of the robot animal; the electroneurographic signal amplification display 9 is configured to observe and monitor an electroneurographic signal of an implanted electrode stimulating the corresponding brain function area of the animal to determine the correctness of the electrode implantation position; and the shadowless lamp 5 is configured to provide illumination for the operation. The intelligent animal operation table of Embodiment 1 is reasonable and compact in structural arrangement and is convenient for the complete implementation of a robot animal experiment.

Embodiment 2

Based on the intelligent animal operation table of Embodiment 1, the instrument cabinet 6 forms a left medical instrument cabinet 61 and a right electrical instrument cabinet 62 which are isolated from each other;

the medical instrument cabinet 61 is configured to store instruments used for craniotomy and electrode implantation operations; and the electrical instrument cabinet 62 is configured to store an electronic device and a circuit welding tool.

Preferably, a cabinet door 63 of the instrument cabinet 6 is a push-pull cabinet door.

Preferably, the instrument cabinet 6 and the operation platform 3 are made of a stainless steel material.

According to the intelligent animal operation table of Embodiment 2, the instrument cabinet 6 is divided into a medical instrument cabinet 61 and an electrical instrument cabinet 62; and a medical instrument and an electrical instrument are separated, so that an appropriate tool is selected in the experiment in a short time, the experimental operation is facilitated, and the animal death caused by the pollution to the medical instrument by the electrical instrument in the operation can be avoided.

Embodiment 3

Based on Embodiment 1 or 2, the intelligent animal operation table further includes an ultraviolet disinfection lamp 7; and the ultraviolet disinfection lamp 7 is fixedly arranged in an upper part of the instrument cabinet 6.

According to the intelligent animal operation table of Embodiment 3, the ultraviolet disinfection lamp 7 can ensure that the operation process can be performed under a relatively aseptic condition.

Embodiment 4

Based on Embodiment 1, 2 or 3, the intelligent animal operation table further includes a body temperature monitor 10; and the body temperature monitor 10 is fixed on the top surface of the operation platform 3 and located below the instrument cabinet 6 and behind the welding table 11.

According to the intelligent animal operation table of Embodiment 4, the body temperature monitor 10 can detect the body temperature of the animal in the operation process, can maximally ensure the survival rate of the experimental animal and can maximally ensure the success rate of the experiment.

Embodiment 5

Based on Embodiments 1 to 4, the intelligent animal operation table further includes a waste storage box 4; and the waste storage box 4 is fixed on a rear part of a left end face of the operation platform 3.

Preferably, the intelligent animal operation table is further provided with a mains power (110V, 220V or 380V) socket 8; and the mains power socket 8 is fixedly arranged on the top surface of the operation platform 3 and located behind the electroneurographic signal amplification display 9 and below the instrument cabinet 6.

According to the intelligent animal operation table of Embodiment 5, medical wastes and electronic wastes generated in the operation experiment process are performed conveniently, and the pollution to the operation platform can be avoided.

Embodiment 6

Figure 2:
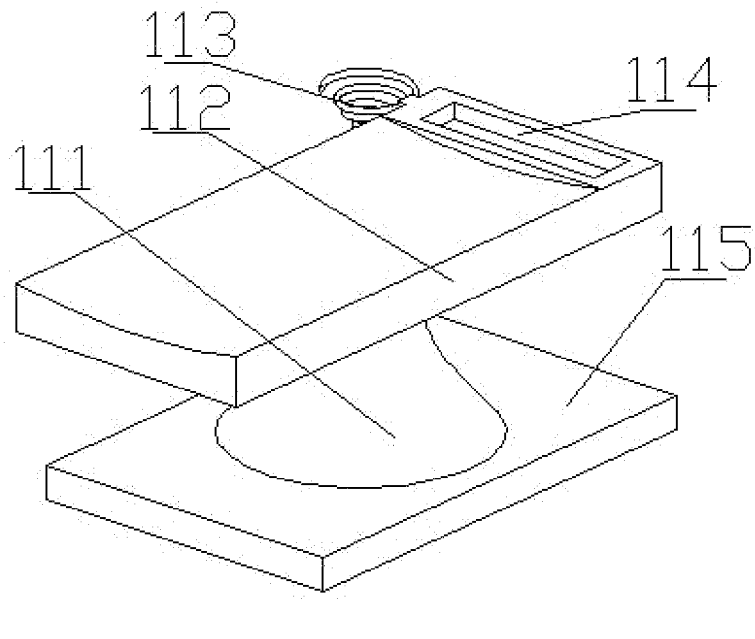
FIG. 2 is a schematic diagram of a three-dimensional structure of a welding table according to an embodiment of an intelligent animal operation table of the present invention.

Based on the intelligent animal operation table of Embodiments 1 to 5, as shown in FIG. 2, the welding table 11 includes a welding rotation base 111, a welding base 115 and a welding platform 112;

the welding base 115 is configured to be attached and fixed to the top surface of the operation platform 3;

an upper end of the welding rotation base 111 is connected to a bottom surface of the welding platform 112, and a lower end of the welding rotation base is connected to the welding base 115;

the welding platform 112 is capable of rotating around a vertical shaft relative to the welding base 115; and a top surface of the welding platform 112 is a concave surface with high front and rear parts and a low middle part.

According to the intelligent animal operation table of Embodiment 6, the welding platform 112 of the welding table 11 adopts a concave surface, and the animals placed on the welding platform 112 are unlikely to slide relatively.

Embodiment 7

According to the intelligent animal operation table of Embodiment 6, an upper end of the welding rotation base 111 is connected to a bottom surface of the welding platform 112, and a lower end of the welding rotation base is connected to a welding base 115, so that the welding platform 112 is fixed on the welding base 115 and can rotate around a vertical shaft relative to the welding base 115.

Preferably, the welding table 11 further includes an electric soldering iron placing rack 113; the electric soldering iron placing rack 113 is fixedly arranged on a rear end face of a right part of the welding platform 112; and a groove 114 is formed in the right part of the welding platform 112, and the groove 114 is used as a rosin pool.

Preferably, the welding platform 112 is capable of rotating 360 degrees around the vertical shaft relative to the welding base 115 through the welding rotation base 111.

Preferably, the welding platform 112 is made of a marble material.

According to the intelligent animal operation table of Embodiment 7, the welding platform 112 is fixed on the welding base 115 and can rotate around the vertical shaft relative to the welding base 115, and an electric soldering iron placing rack 113 and a groove 114 serving as a rosin pool are designed, so that experimenters can perform circuit welding efficiently.

Embodiment 8

Based on Embodiments 1 to 7, the intelligent animal operation table further includes a platform rotation base 2 and a base 1; and a bottom surface of the operation platform 3 is connected to the base 1 through the platform rotation base 2.

Preferably, the operation platform 3 is capable of rotating 270 degrees around the vertical shaft relative to the base 1 through the platform rotation base 2;

Preferably, the physiological signal acquisition system 12 has 16 channels.

Preferably, the brain stereotaxic instrument 13 and the welding base 115 are fixed on the operation platform 3 through a bolt 131.

The above descriptions are only preferred embodiments of the present invention, and are not intended to limit the present invention. Any modifications, equivalent replacements, etc. made within the spirit and principles of the present invention shall be included in the protection scope of the present invention.

What is claimed is:

1. An intelligent animal operation table, comprising:
an operation platform, an instrument cabinet, a brain stereotaxic instrument, a physiological signal acquisition system, a welding table, an electroneurographic signal amplification display, and a shadowless lamp,
wherein the instrument cabinet is a cuboid, and a left end and a right end of a bottom surface of the instrument cabinet are fixed at a left end and a right end of a rear part of a top surface of the operation platform respectively through supporting columns;
the brain stereotaxic instrument is fixed on a left part of the top surface of the operation platform and located on a front side of the instrument cabinet;
the physiological signal acquisition system is fixed on the left part of the top surface of the operation platform and located below the instrument cabinet and behind the brain stereotaxic instrument;
the welding table is fixed on the top surface of the operation platform and located on the front side of the instrument cabinet and a right side of the physiological signal acquisition system;

the electroneurographic signal amplification display is fixed on a right part of the top surface of the operation platform, located on the front side of the instrument cabinet and on a right rear side of the welding table, and configured to be in signal connection with an electroneurographic signal sensor of a corresponding brain function area of an animal; and
the shadowless lamp is fixed on a right part of a top surface of the instrument cabinet.

2. The intelligent animal operation table according to claim 1, wherein
the instrument cabinet forms a left medical instrument cabinet and a right electrical instrument cabinet which are isolated from each other;
the medical instrument cabinet is configured to store instruments used for craniotomy and electrode implantation operations; and
the electrical instrument cabinet is configured to store an electronic device and a circuit welding tool.

3. The intelligent animal operation table according to claim 1, further comprising:
an ultraviolet disinfection lamp,
wherein the ultraviolet disinfection lamp is fixedly arranged in an upper part of the instrument cabinet.

4. The intelligent animal operation table according to claim 1, further comprising:
a body temperature monitor,
wherein the body temperature monitor is fixed on the top surface of the operation platform and located below the instrument cabinet and behind the welding table.

5. The intelligent animal operation table according to claim 1, further comprising:
a waste storage box,
wherein the waste storage box is fixed on a rear part of a left end face of the operation platform.

6. The intelligent animal operation table according to claim 1, further comprising:
a mains power socket,
wherein the mains power socket is fixedly arranged on the top surface of the operation platform and located behind the electroneurographic signal amplification display and below the instrument cabinet.

7. The intelligent animal operation table according to claim 1, wherein
the welding table comprises a welding rotation base, a welding base and a welding platform;
the welding base is configured to be attached and fixed to the top surface of the operation platform;
an upper end of the welding rotation base is connected to a bottom surface of the welding platform, and a lower end of the welding rotation base is connected to the welding base;
the welding platform is capable of rotating around a vertical shaft relative to the welding base; and
a top surface of the welding platform is a concave surface with high front and rear parts and a low middle part.

8. The intelligent animal operation table according to claim 7, wherein
the welding table further comprises an electric soldering iron placing rack;
the electric soldering iron placing rack is fixedly arranged on a rear end face of a right part of the welding platform; and
a groove is formed in the right part of the welding platform, and the groove is used as a rosin pool.

9. The intelligent animal operation table according to claim 8, further comprising:

a platform rotation base and a base, wherein a bottom surface of the operation platform is connected to the base through the platform rotation base.

10. The intelligent animal operation table according to claim 9, wherein the operation platform is capable of rotating 270 degrees around the vertical shaft relative to the base through the platform rotation base;

the physiological signal acquisition system has 16 channels;

a cabinet door of the instrument cabinet is a push-pull cabinet door;

the instrument cabinet and the operation platform are made of a stainless steel material;

the welding platform is capable of rotating 360 degrees around the vertical shaft relative to the welding base through the welding rotation base; and the welding platform is made of a marble material.

* * * * *